United States Patent [19]

Suzue et al.

[11] Patent Number: 4,846,991

[45] Date of Patent: Jul. 11, 1989

[54] NOVEL FATTY ACID-LACTIC ACID ESTER

[75] Inventors: Shigetoshi Suzue; Akio Kimura; Kiyoshi Tsukada; Kozo Noda, all of Wakayama; Hidekazu Ogino, Tokyo; Jun Kamegai, Ichikawa, all of Japan

[73] Assignee: Kao Corporation, Tokyo, Japan

[21] Appl. No.: 152,493

[22] Filed: Feb. 5, 1988

[30] Foreign Application Priority Data

Feb. 12, 1987 [JP] Japan .................................. 62-30514

[51] Int. Cl.$^4$ .......................... C11D 1/00; C11C 3/00; A61K 7/06; C07C 69/52
[52] U.S. Cl. .............................. 252/89.1; 252/DIG. 5; 252/DIG. 13; 252/DIG. 14; 260/410.6; 260/410.9 R; 560/205; 560/224; 560/129; 424/70
[58] Field of Search ....... 252/89.1, DIG. 5, DIG. 13, 252/DIG. 14; 260/410.6, 410.9 R; 560/205, 224, 129; 424/70

[56]  References Cited

U.S. PATENT DOCUMENTS

| | | | |
|---|---|---|---|
| 2,733,252 | 1/1956 | Thompson et al. | 260/410.6 |
| 2,789,992 | 4/1957 | Thompson et al. | 260/410.9 |
| 3,098,795 | 7/1963 | Kreps | 252/89.1 |
| 3,728,447 | 4/1973 | Osipow et al. | 252/DIG. 13 |
| 4,012,341 | 3/1977 | Orshitzer | 252/174 |
| 4,029,606 | 6/1977 | Isa et al. | 252/89.1 |
| 4,134,970 | 1/1979 | Panke et al. | 252/DIG. 13 |
| 4,198,311 | 4/1980 | France et al. | 252/89.1 |

*Primary Examiner*—Paul Lieberman
*Assistant Examiner*—Helene Kirschner
*Attorney, Agent, or Firm*—Oblon, Spivak, McClelland, Maier & Neustadt

[57] ABSTRACT

Lactic acid esters of an α-branched fatty acid possessing an excellent hair conditioning effect are disclosed. Typical example is sodium 2-heptylundecanoyl acid lactate prepared by the reaction of 2-heptylundecanoic acid and lactic acid in the presence of an alkali such as sodium hydroxide. This compound gives a shampoo composition in conjunction with an anionic surface active agent, and a hair rinse composition when a quaternary ammonium salt is formulated. The compositions have excellent conditioning effects on use such as good slipperiness and hair curling formation or retention performance.

19 Claims, No Drawings

NOVEL FATTY ACID-LACTIC ACID ESTER

1. Field of Invention

This invention relates to a novel fatty acid-lactic acid ester and, more particularly, to a lactic acid ester of α-branched fatty acid which possesses an excellent hair conditioning effect and can be used as toiletries.

2. Description of the Background

Since lactic acid esters of fatty acids function to produce an antiseptic effect, emulsion formation, detergency, and the like, and can be absorbed by proteins, they are used in foods, shampoos, cosmetics, or the like. Stearoyl lactic acid salts (sodium or potassium salt) which are linear fatty acid esters, for example, are known to be capable of ensuring soft-baked bread, and of providing an anti-aging effect. These compounds are used as a bread substrate improver. In addition to these lactic acid esters of a linear fatty acid, lactic acid esters having an acyl group of iso-stearic acid with a methyl group as a branched chain, which are produced as by-products in the production of dimer acids, are also used for shampoos and cosmetics as agents producing the effects of detergency, emulsification, and conditioning.

In this way, the above-mentioned lactic acid ester of iso-stearic acid, which is a by-product of dimer acid production processes, or the like, are presently used as hair cosmetics such as shampoos and rinse, relying on its hair conditioning effect due to its ability to absove proteins. The conditioning effect of these esters, however, is not yet satisfactory in view of the tangling feeling when hair is combed or an incompletely finished feeling after washing due to the absence of dampishness.

The inventors have conducted extensive studies to obtain a compound which provides an excellent hair conditioning effect, and found that lactic acid esters of fatty acids having a branched chain at the α-position, represented by formula (I) which follows, exhibit this hair conditioning effect. Such a finding has led to the completion of this invention.

SUMMARY OF THE INVENTION

Accordingly, an object of this invention is to provide a fatty acid-lactic acid ester represented by the formula:

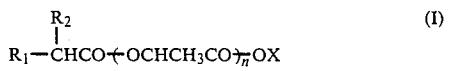
 (I)

which $R_1$ and $R_2$ independently represent alkyl groups of a $C_{4-18}$ carbon atom content, X represents a hydrogen atom, alkali metal, alkaline earth metal, ammonium group, alkanol ammonium group, or lower alkyl ammonium group, and n represents a value of 1 to 5.

Another object of the invention is to provide a shampoo composition comprising as essential components the fatty acid-lactic acid ester of the above formula (I) and an anionic surface active agent.

Still another object of the invention is to provide a rinse composition comprising as essential components the fatty acid-lactic acid ester of the above formula (I) and a quarternary ammonium salt.

Other objects, features, and advantages of this invention will appear more fully from the following description.

DETAILED DESCRIPTION OF THE INVENTION AND PREFERRED EMBODIMENTS

In fatty acid-lactic acid esters of this invention represented by the formula (I), the acyl group of

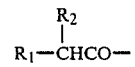

may be 2-butyloctanoyl group, 2-butyltetradecanoyl group, 2-hexyldecanoyl group, 2-heptylundecanoyl group, 2-octyldecanoyl group, 2-decyltetradecanoyl group, 2-decyloctadecanoyl group, 2-tetradecyloctadecanoyl group, 2-hexadecyleicosanoyl group, or the like. Among these, those containing 14 to 32 carbon atoms are preferable.

Further, particularly preferable fatty acid-lactic acid esters are those containing an acyl group of the formula:

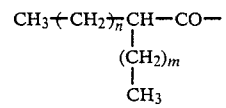

in which n has a value of 5 to 15 and m has a value of 3 to 14.

The n value in formula (I) represents the average numbers of lactic radicals $-(OCHCH_3CO)-$, and is preferably 1 to 3.

Fatty acid-lactic acid esters of this invention can be prepared according to methods known in the art. For example, they are easily prepared by reacting a fatty acid of a suitable structure and carbon atom content with lactic acid in the presence of an alkali such as sodium hydroxide, potassium hydroxide, sodium carbonate, or the like, at 140 to 220° C. for 4 to 10 hours while eliminating formed water, and, as required, by converting the free acids thus obtained into various kinds of salts. In this reaction, an n mole amount of lactic acid [n is the number in formula (I)] is charged to the reaction system and reacted with one mole of fatty acid, using usually an alkali of one mole.

A 50% or 90% aqueous lactic acid solution available in the market may be used as a starting raw material for this reaction. Such an aqueous lactic acid solution, if heated to a temperature of 180° C. to 220° C., is readily converted by dehydration-condensation to condensed lactic acid. Such condensed lactic acid can also be used as a raw material.

As a fatty acid, which is another starting raw material for deriving the esters of this invention, commercially available fatty acids can be used such as, for example, 2-heptylundecanoic acid (Trade Name: Diadol 18GA, manufactured by Mitsubishi Chemical Industries, Ltd.) which is obtained by oxidation of Guerbet alcohol, 2-(1,3,3-trimethylbutyl)-5,7,7-trimethyloctanoic acid (Tradename: Iso-stearic acid, manufactured by Nissan Chemical Co., Ltd.) derived by oxidation of an aldol condensate, and the like. Fatty acids to be used, however, are not limited to those mentioned above. Various fatty acids with a variety of carbon atom contents and prepared by diversified methods can be used as raw materials.

The fatty acid-lactic acid esters of this invention can be formulated in shampoo compositions and hair rinse compositions. Examples of preferred formulations are as follows:

| Shampoo compositions | |
|---|---|
| (A) Fatty acid-lactic acid esters | 0.1–5% by weight |
| (B) Anionic surface active agents | 5–50% by weight |

Examples of anionic surface active agents to be used as component (B) of these compositions are salts of alkylbenzene sulfonic acids having alkyl groups of an average 10 to 16 carbon atom content, salts of sulfuric acid esters of higher alcohols having an average 8 to 18 carbon atom content, salts of sulfuric acid esters of polyoxyalkylene (an average 1 to 10 mole adduct of $C_2$ or $C_3$ alkylene oxide) adducts of higher alcohols having an average 8 to 18 carbon atom content, salts of $\alpha$-olefin sulfonates with an average 8 to 18 carbonatom content, salts of alkyl phosphates with an average 8 to 18 carbon atom content, and the like. A counter ion of these anionic surface active agents is selected from the group consisting of alkali metals, alkaline earth metals, ammonium, and alkanol amines of a $C_2$ or $C_3$ carbon atom content.

Known components for conventional shampoos may be formulated in the shampoo compositions of this invention as required in the amount not impairing the effect of this invention. Such known components include, for example, amphoteric or nonionic surface active agents, solubilizing agents such as propylene glycol, glycerol, urea, and the like, viscosity controlling agents such as ethyl alcohol, isopropyl alcohol, hydroxyethyl cellulose, methyl cellulose, higher alcohols, and the like, perfumes, coloring agents, ultraviolet absorbers, antioxidants, antiseptics, pearly agents, and the like.

| Hair rinse compositions | |
|---|---|
| (A) Fatty acid-lactic acid esters | 0.1–5% by weight |
| (C) Salts of quaternary ammonium | 0.1–10% by weight |

Preferable salts of quaternary ammonium to be used as the component (C) are compounds represented by formula (II):

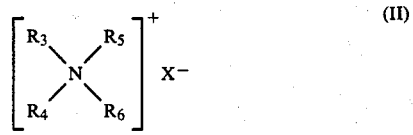

$$\left[ \begin{array}{cc} R_3 & R_5 \\ \diagdown & \diagup \\ & N \\ \diagup & \diagdown \\ R_4 & R_6 \end{array} \right]^+ \quad X^- \tag{II}$$

which one or two radicals among from $R_3$–$R_6$ represent long-chained alkyl or hydroxyalkyl groups each having 8 to 22 carbon atoms, with the remaining radicals being alkyl or hydroxyalkyl groups each having 1 to 3 carbon atoms, or benzyl groups, and X represents a halogen atom or an alkyl sulfate group of a 1 or 2 carbon atom content. Various additives commonly used for hair treatment agents may be added to this hair rinse composition to the extent that its intended effect may not be impaired. Such additives include oils or fats such as fatty acids, higher alcohol, oil or fat esters of lanolin, liquid paraffin, and the like, surface active agents such as nonionic surface active agents, amphoteric surface active agents, and the like, disinfectants, vehicles, perfumes, coloring agents, and the like. In particular, the addition of hydrocarbons with molecular weights of 100 to 700, such as liquid and solid paraffin, in the amount of 0.1 to 10% will enhance softness of hair treated by these hair rinse compositions.

Fatty acid-lactic acid esters prepared as illustrated above not only possess excellent dehydration resistance in themselves, but also, when applied to hair or skin, produce an easiness or readiness of handling, and improve such conditioning effects as slipperiness and hair curling formation or retention performance. The compounds of this invention, therefore, may find wide application in the toiletry field as ingredients for shampoos, rinses, treatments, creams, and the like.

Other features of the invention will become apparent in the course of the following description of the exemplary embodiments which are given for illustration of the invention and are not intended to be limiting thereof.

EXAMPLES

Example 1

To a 1 liter 4-necked flask were charged 287 gm of 2-heptylundecanoic acid, 148 gm of 90% lactic acid, and 45 gm of sodium carbonate. Following a temperature increase while feeding nitrogen gas, an esterification reaction was effected at 180° C. for 5 hours to obtain 415 gm of an amber, slightly viscous liquid of sodium 2-heptylundecanoyl acid lactate [the compound in which $R_1 = C_9H_{19}$, $R_2 = C_7H_{15}$, n = 1.5, and X = Na in formula (I)].

Analysis of this compound revealed that it had a saponification value of 216.8 mg/KOH (after having been saponified for 3 hours), an acid value of 62.1 mg/KOH, a hydroxyl value of 35.5 mg/KOH, an Na content of 4.7%, a viscosity of 580 cp (at 100° C.), and a specific gravity of 0.948 (at 100° C.).

EXAMPLES 2–7

In these examples, the raw materials listed in Table 1 were reacted under the reaction conditions noted to give the compounds summarized Table 2.

TABLE 1

| | | Amounts of Raw Materials (gm) | | | Reaction Temp. (°C.) | Reaction Time (hour) |
|---|---|---|---|---|---|---|
| Examples | Fatty acid | | Lactic acid | Na$_2$CO$_3$ | | |
| No. 2 | 2-butyloctanoic acid | 200 | 149 | 36 | 200 | 5 |
| No. 3 | 2-(1,3,3-trimethyl butyl)-5,7,7-trimethyl octanoic acid | 284 | 199 | 45 | 200 | 5 |
| No. 4 | 2-octyldecanoic acid | 292 | 148 | 46 | 180 | 5 |
| No. 5 | 2-heptylundecanoic acid | 284 | 268* | 45 | 180 | 5 |
| No. 6 | 2-decyldodecanoic acid | 456 | 147 | 53 | 180 | 5 |
| No. 7 | 2-decyloctadecanoic acid | 562 | 147 | 53 | 180 | 5 |

*50% lactic acid

TABLE 2

| Esters prepared in Example | Saponification Value | Acid Value | Hydroxyl Value | Degree of Condensation (n) | Yield (gm) |
|---|---|---|---|---|---|
| No. 2 | 282.2 | 60.4 | 19.3 | 1.5 | 317 |
| No. 3 | 187.3 | 65.1 | 41.8 | 2.0 | 460 |
| No. 4 | 211.6 | 66.2 | 40.7 | 1.5 | 423 |
| No. 5 | 218.3 | 72.9 | 43.7 | 1.5 | 408 |
| No. 6 | 137.7 | 53.5 | 45.4 | 1.5 | 601 |
| No. 7 | 123.7 | 37.8 | 26.1 | 1.5 | 654 |

EXAMPLE 8

The shampoo compositions in Table 3 were prepared according to a conventional method. Each shampoo composition was subjected to testing, in which human hair weighing 30 gm retaining 20 gm of water at 40° C. therein was washed with 1 gm of the shampoo composition. Lathering, cleansing ability, and the like of the composition were evaluated by expert panelists. The results are shown in Table 3. In this test, the following standards were applied to the composition evaluation.

Slipperiness of lather during washing:
AAA: lather is very slippery
BBB: lather is fairly slippery and does not adhere to the fingers
CCC: slipperiness of lather is normal
DDD: slipperiness of lather is inadequate causing the hair to tangle around the fingers and be brittle.

Feeling of lather during washing:
AAA: lather is abundant and creamy
BBB: lather is abundant, but not creamy
CCC: the amount of lather is adequate, but lather is coarse
DDD: lather is light and coarse Slipperiness of hair after having been dried:
AAA: of hair after having been dried:
BBB: hair is moderately slippery
CCC: hair is slightly slippery
DDD: hair is not slippery but is rather brittle feelings Glossiness of hair after having been dried:
AAA: glossiness of hair is clearly observed
BBB: hair appears glossy
CCC: hair appears slightly glossy
DDD: hair is not glossy.

In the tables below, the figures of various ingredients for various compositions are expressed in % by weight. The compositions the numbers of which are asterisked are those of the present invention, and others represent comparative compositions.

TABLE 3

| | Composition Nos. | | | | | | | | |
|---|---|---|---|---|---|---|---|---|---|
| | 1 | 2* | 3* | 4* | 5* | 6* | 7* | 8* | 9 |
| triethanolamine lauryl sulfate | 20 | 20 | 20 | 20 | 20 | 20 | 20 | 20 | 20 |
| diethanol amide of coconut oil fatty acid | 3 | 3 | 3 | 3 | 3 | 3 | 3 | 3 | 3 |
| Ester prepared in Example 1 | — | 2 | — | — | — | — | — | — | — |
| Ester prepared in Example 2 | — | — | 2 | — | — | — | — | — | — |
| Ester prepared in Example 3 | — | — | — | 2 | — | — | — | — | — |
| Ester prepared in Example 4 | — | — | — | — | 2 | — | — | — | — |
| Ester prepared in Example 5 | — | — | — | — | — | 2 | — | — | — |
| Ester prepared in Example 6 | — | — | — | — | — | — | 2 | — | — |
| Ester prepared in Example 7 | — | — | — | — | — | — | — | 2 | — |
| stearoyl lactylate (comparative product) | — | — | — | — | — | — | — | — | 2 |
| ion exchanged water | 77 | 75 | 75 | 75 | 75 | 75 | 75 | 75 | 75 |
| Lathering Characteristics | | | | | | | | | |
| Slipperiness | DDD | BBB | CCC | BBB | AAA | AAA | AAA | AAA | CCC |
| Creaminess | DDD | BBB | CCC | CCC | BBB | BBB | BBB | BBB | DDD |
| Finish | | | | | | | | | |
| Slipperiness | DDD | AAA | BBB | BBB | AAA | AAA | AAA | AAA | CCC |
| Gloss | DDD | BBB | BBB | BBB | AAA | BBB | BBB | AAA | DDD |

EXAMPLE 9

Shampoo compositions noted in Table 4 were prepared and were evaluated in the same manner as those in Example 8. The results are shown in Table 4. In this table and tables that follows, "POE" stands for polyoxyethylene and the number in parenthesis immediately following "POE" designates the average number of moles of ethylene oxide in the polyoxyethlene.

TABLE 4

| | Composition Nos. | | | | | | | | |
|---|---|---|---|---|---|---|---|---|---|
| | 10 | 11* | 12* | 13* | 14* | 15* | 16* | 17* | 18 |
| POE(3) sodium lauryl sulfate | 20 | 20 | 20 | 20 | 20 | 20 | 20 | 20 | 20 |
| diethanol amide | 3 | 3 | 3 | 3 | 3 | 3 | 3 | 3 | 3 |

TABLE 4-continued

|  | Composition Nos. | | | | | | | | |
| --- | --- | --- | --- | --- | --- | --- | --- | --- | --- |
|  | 10 | 11* | 12* | 13* | 14* | 15* | 16* | 17* | 18 |
| of coconut oil fatty acid |  |  |  |  |  |  |  |  |  |
| Ester prepared in Example 1 | — | 2 | — | — | — | — | — | — | — |
| Ester prepared in Example 2 | — | — | 2 | — | — | — | — | — | — |
| Ester prepared in Example 3 | — | — | — | 2 | — | — | — | — | — |
| Ester prepared in Example 4 | — | — | — | — | 2 | — | — | — | — |
| Ester prepared in Example 5 | — | — | — | — | — | 2 | — | — | — |
| Ester prepared in Example 6 | — | — | — | — | — | — | 2 | — | — |
| Ester prepared in Example 7 | — | — | — | — | — | — | — | 2 | — |
| stearoyl lactylate (comparative product) | — | — | — | — | — | — | — | — | 2 |
| ion exchanged water | 77 | 75 | 75 | 75 | 75 | 75 | 75 | 75 | 75 |
| Lathering Characteristics |  |  |  |  |  |  |  |  |  |
| Slipperiness | DDD | BBB | BBB BBB | BBB | AAA | AAA | AAA | AAA | CCC |
| Creaminess | DDD | BBB | CCC | CCC | BBB | BBB | BBB | BBB | DDD |
| Finish |  |  |  |  |  |  |  |  |  |
| Slipperiness | DDD | AAA | BBB | BBB | BBB | AAA | AAA | AAA | CCC |
| Gloss | DDD | BBB | BBB | BBB | BBB | BBB | BBB | AAA | DDD |

EXAMPLE 10

Shampoo compositions in Table 5 were prepared and evaluated in the same manner as in Example 8. The results are shown in Table 5.

TABLE 5

|  | Composition Nos. | | | | | | | |
| --- | --- | --- | --- | --- | --- | --- | --- | --- |
|  | 19 | 20* | 21* | 22* | 23* | 24* | 25 | 26 |
| triethanolamine monolauryl phosphate | 20 | 20 | 20 | 20 | 20 | 20 | 20 | 20 |
| diethanol amide of coconut oil fatty acid | 3 | 3 | 3 | 3 | 3 | 3 | 3 | 3 |
| Ester prepared in Example 1 | — | 2 | — | — | — | — | — | — |
| Ester prepared in Example 2 | — | — | 2 | — | — | — | — | — |
| Ester prepared in Example 3 | — | — | — | 2 | — | — | — | — |
| Ester prepared in Example 4 | — | — | — | — | 2 | — | — | — |
| Ester prepared in Example 5 | — | — | — | — | — | 2 | — | — |
| stearoyl lactylate (comparative product) | — | — | — | — | — | — | 2 | — |
| methyl-branched isostearoyl lactylate (comparative product) | — | — | — | — | — | — | — | 2 |
| ion exchanged water | 77 | 75 | 75 | 75 | 75 | 75 | 75 | 75 |
| Lathering Characteristics |  |  |  |  |  |  |  |  |
| Slipperiness | DDD | AAA | BBB | BBB | AAA | AAA | CCC | CCC |
| Creaminess | DDD | AAA | BBB | CCC | BBB | BBB | DDD | CCC |
| Finish |  |  |  |  |  |  |  |  |
| Slipperiness | DDD | AAA | BBB | BBB | AAA | BBB | CCC | CCC |
| Gloss | DDD | AAA | BBB | CCC | AAA | BBB | DDD | DDD |

EXAMPLE 11

Hair rinse compositions of formulations shown in Table 6 were prepared. Hair bundles each weighing 30 gm were washed using a plane shampoo and rinsed in the same manner as in Example 8. To each hair bundle the hair rinse compositions of 1 gm each were applied, which was rinsed again, and dried. Each bundle was subjected to organoleptic evaluation to determine product satisfaction by expert panelist. The results shown in Table 6 were obtained using the following standards for evaluating the compositions.

Slippery feelings:
AAA: slippery
BBB: slightly slippery
CCC: not slippery
Dampishness:
AAA: felt wet or dampish
BBB: slightly wet or dampish
CCC: not wet or dampish
Softness:
AAA: soft
BBB: slightly soft
CCC: not soft

TABLE 6

| | Composition Nos. | | | | | | | | |
|---|---|---|---|---|---|---|---|---|---|
| | 27 | 28* | 29* | 30* | 31* | 32* | 33* | 34* | 35 |
| stearyl trimethyl ammonium chloride | 1.2 | 1.2 | 1.2 | 1.2 | 1.2 | 1.2 | 1.2 | 1.2 | 1.2 |
| stearyl alcohol | 2 | 2 | 2 | 2 | 2 | 2 | 2 | 2 | 2 |
| hydroxyethyl cellulose | — | — | — | — | — | — | 0.3 | 0.3 | — |
| Ester prepared in Example 1 | — | 1 | — | — | — | — | — | — | — |
| Ester prepared in Example 2 | — | — | 1 | — | — | — | — | — | — |
| Ester prepared in Example 3 | — | — | — | 1 | — | — | — | — | — |
| Ester prepared in Example 4 | — | — | — | — | 1 | — | — | — | — |
| Ester prepared in Example 5 | — | — | — | — | — | 1 | — | — | — |
| Ester prepared in Example 6 | — | — | — | — | — | — | 0.5 | — | — |
| Ester prepared in Example 7 | — | — | — | — | — | — | — | 0.5 | — |
| stearoyl lactylate (comparative product) | — | — | — | — | — | — | — | — | 1 |
| ion exchanged water | 96.8 | 95.8 | 95.8 | 95.8 | 95.8 | 95.8 | 96.0 | 96.0 | 95.8 |
| Slipperiness | CCC | AAA | AAA | AAA | AAA | AAA | AAA | AAA | BBB |
| Dampishnsss | CCC | AAA | CCC | BBB | AAA | AAA | AAA | AAA | CCC |
| Softness | CCC | AAA | BBB | BBB | AAA | AAA | AAA | AAA | BBB |

EXAMPLE 12

Creams with formulations shown in Table 7 were prepared and applied to arms of expert panelists to evaluate the same according to the standards. The results are shown in Table 7.

Stickilessness:
AAA: neat and refreshed
BBB: slightly sticky
CCC: sticky
Wetness or dampishness
AAA: dampish
BBB: slightly dampish
CCC: not dampish

TABLE 7

| | Composition Nos. | | | | | | |
|---|---|---|---|---|---|---|---|
| | 36 | 37* | 38* | 39* | 40* | 41* | 42 |
| liquid paraffin | 13 | 13 | 13 | 13 | 13 | 13 | 13 |
| Tween 60 | 5 | 5 | 5 | 5 | 5 | 5 | 5 |
| Leodol MS 60 | 1 | 1 | 1 | 1 | 1 | 1 | 1 |
| hydrogenated castor oil | 2 | 2 | 2 | 2 | 2 | 2 | 2 |
| Ester prepared in Example 1 | — | 2 | — | — | — | — | — |
| Ester prepared in Example 2 | — | — | 2 | — | — | — | — |
| Ester prepared in Example 3 | — | — | — | 2 | — | — | — |
| Ester prepared in Example 4 | — | — | — | — | 2 | — | — |
| Ester prepared in Example 5 | — | — | — | — | — | 2 | — |
| stearoyl lactylate (comparative product) | — | — | — | — | — | — | 2 |
| ion exchanged water | 79 | 77 | 77 | 77 | 77 | 77 | 77 |
| Feelings when creams were applied | | | | | | | |
| Stikilessness | CCC | AAA | BBB | BBB | AAA | AAA | CCC |
| Dampishness | CCC | AAA | AAA | AAA | AAA | AAA | CCC |

EXAMPLE 13

Shampoo compositions of Table 8 were prepared and evaluated in the same manner as in Example 8. The results are shown in Table 8.

TABLE 8

| | Composition Nos. | | | |
|---|---|---|---|---|
| | 43 | 44* | 45* | 46* |
| POE (2.5) laurylether sulfate | 15 | 15 | 15 | 15 |
| coconut oil fatty acid diethanol amide | 5 | 5 | 5 | 5 |
| Ester prepared in Example 4 | 0.01 | 0.1 | 1.0 | 2.0 |
| Emanon 3299R (polyoxyethylene distearate) | 1.2 | 1.2 | 1.2 | 1.2 |
| citric acid | 0.5 | 0.5 | 0.5 | 0.5 |
| methyl paraben | 0.1 | 0.1 | 0.1 | 0.1 |
| perfume | small amount | small amount | small amount | small amount |
| coloring agent | small amount | small amount | small amount | small amount |
| ion exchanged water | balance | balance | balance | balance |
| Feelings of lather | | | | |
| Slippery feeling | BBB | AAA | AAA | BBB |
| Creamy feeling | CCC | AAA | AAA | BBB |
| Finishness | | | | |
| Slipperiness | CCC | AAA | AAA | BBB |
| Gloss | BBB | AAA | AAA | AAA |

EXAMPLE 14

Shampoo compositions of Table 9 were prepared and evaluated in the same manner as in Example 8. The results are shown on Table 9.

TABLE 9

| | Composition Nos. | | | |
|---|---|---|---|---|
| | 47 | 48* | 49* | 50* |
| triethanolamine lauryl sulfate | 20 | 20 | 20 | 20 |
| coconut oil fatty acid diethanol amide | 5 | 5 | 5 | 5 |
| Ester prepared in Example 4 | 0.01 | 0.1 | 1.0 | 2.0 |
| Methorose 60 SH1000 (methyl cellulose) | 0.5 | 0.5 | 0.5 | 0.5 |
| urea | 6 | 6 | 6 | 6 |
| perfume | small amount | small amount | small amount | small amount |
| coloring agent | small amount | small amount | small amount | small amount |
| ion exchanged water | balance | balance | balance | balance |
| Feelings of lather | | | | |
| Slippery feeling | BBB | BBB | AAA | BBB |
| Creamy feeling | CCC | BBB | AAA | BBB |
| Finishness | | | | |
| Slipperiness | CCC | AAA | AAA | BBB |
| Gloss | CCC | AAA | AAA | AAA |

EXAMPLE 15

The Hair rinse compositions of Table 10 were prepared and evaluated in the same manner as in Example 11. The results are shown on Table 10.

TABLE 10

| | Composition Nos. | | | |
|---|---|---|---|---|
| | 51 | 52* | 53* | 54* |
| stearyl trimethyl ammonium chloride | 1.2 | 1.2 | 1.2 | 1.2 |
| stearyl alcohol | 2 | 2 | 2 | 2 |
| Ester prepared in Example 4 | 0.01 | 0.1 | 1.0 | 2.0 |
| Cellosize QP52000 (hydroxyethyl cellulose) | 0.3 | 0.3 | 0.3 | 0.3 |
| perfume | small amount | small amount | small amount | small amount |
| coloring agent | small amount | small amount | small amount | small amount |
| ion exchanged water | balance | balance | balance | balance |
| Slippery feeling | CCC | BBB | BBB | BBB |
| Dampishness | DDD | CCC | BBB | BBB |
| Softness | DDD | CCC | BBB | BBB |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A fatty acid-lactic acid ester represented by the formula:

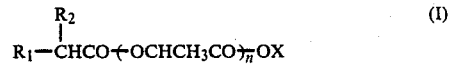

in which $R_1$ and $R_2$ independently represent alkyl groups of a $C_{4-18}$ carbon atom content, X represents a hydrogen atom, alkali metal, alkaline earth metal, ammonium group, alkanol ammonium group, or lower alkyl ammonium group, and n represents a value of 1 to 5.

2. A shampoo composition comprising:
(A) 0.1 5% by weight of a fatty acid-lactic acid ester represented by the formula:

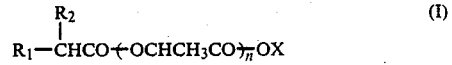

in which Rphd 1 and $R_2$ independently represent alkyl groups of a $C_{4-18}$ carbon atom content, X represents a hydrogen atom, alkali metal, alkaline earth metal, ammonium group, alkanol ammonium group, or lower alkyl ammonium group, and n represents a value of 1 to 5; and
(B) 5 to 50% by weight of an anionic surface active agent.

3. A hair rinse composition comprising:
(A) 0.1 to 5% by weight of a fatty acid-lactic acid ester represented by the formula:

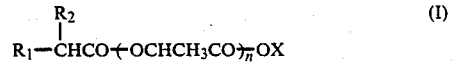

in which $R_1$ and $R_2$ independently represent alkyl groups of a $C_{4-18}$ carbon atom content, X represents a hydrogen atom, alkali metal, alkaline earth metal, ammonium group, alkanol ammonium group, or lower alkyl ammonium group, and n represents a value of 1 to 5; and (C) 0.1 to 10% by weight of a quaternary ammonium salt.

4. The fatty acid-lactic acid ester of claim 1, wherein n is 1–3.

5. The fatty acid-lactic ester of claim 1, wherein the acyl group $R_1R_2CHCO-$ in formula (I) is selected from the group consisting of 2-butyloctanoyl, 2-butyltetradecanoyl, 2-hexyldecanoyl, 2-heptylundecanoyl, 2-octyldecanoyl, 2-decytetradecanoyl, 2-decyloctadecanoly, 2-tetradecyloctadecanoyl and 2-hexadecyleicosanoyl groups.

6. The fatty acid-lactic acid ester of claim 1, wherein said acyl group $R_1R_2CHCO-$ comprising 14–32 carbon atoms.

7. The fatty acid-lactic acid ester of claim 1, wherein said acyl group $R_1R_2CHCO-$ has the formula

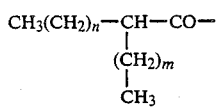

wherein n has a value of 5–15 and m has a value of 3–14.

8. The shampoo composition of claim 2, wherein n is 1–3.

9. The shampoo composition of claim 2, wherein the acyl group $R_1R_2CHCO-$ in formula (I) is selected from the group consisting of 2-butyloctanoyl, 2-butyltetradecanoyl, 2-hexyldecanoyl, 2-heptylundecanoyl, 2-octyldecanoyl, 2-decyltetradecanoyl, 2-decyloctadecanoyl, 2-tetradecyloctadecanoyl and 2-hexadecyleicosanoyl groups.

10. The shampoo composition of claim 2, wherein said acyl group $R_1R_2CHCO-$ comprising 14–32 carbon atoms.

11. The shampoo composition of claim 2, wherein said acyl group $R_1R_2CHCO-$ has the formula

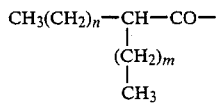

wherein n has a value of 5–15 and m has a value of 3–14.

12. The shampoo composition of claim 2, wherein said anionic surface active agent is selected from the group consisting of salts of alkylbenzene sulfonic acids having alkyl groups of an average 10–16 carbon atoms, salts of sulfuric acid esters of higher alcohols having an average 8–18 carbon atoms, salts of sulfuric acid esters of polyoxyalkylene adducts of higher alcohols having an average of 8–18 carbon atoms, salts of $\alpha$-olefin sulfonates with an average of 8–18 carbon atoms and salts of alkyl phosphates with an average of 8–18 carbon atoms.

13. The shampoo composition of claim 12, wherein said polyoxyalkylene of said salts of sulfuric acid esters of polyoxyalkylene adducts of higher alcohols, comprises an average of 1–10 $C_{2-3}$ alkyleneoxide units.

14. The shampoo composition of claim 2, wherein said anionic surface active agent comprises a counterion selected from the group consisting of alkali metals, alkaline earth metals, ammonium, and $C_2$–$C_3$ alkanol amines.

15. The hair rinse composition of claim 3, wherein n is 1–3.

16. The hair rinse composition of claim 3, wherein the acyl group $R_1R_2CHCO-$ in formula (I) is selected from the group consisting of 2-butyloctanoyl, 2-butyltetradecanoyl, 2-hexldecanoyl, 2-heptylundecanoyl, 2-octyldecanoyl, 2-decyletetradecanoyl, 2-decyloctadecanoyl, 2-tetradecyloctadecanoyl and 2-hexadecyleicosanoyl groups.

17. The hair rinse composition of claim 3, wherein said acyl group $R_1R_2CHCO-$ comprising 14–32 carbon atoms.

18. The hair rinse composition of claim 3, wherein said acyl group $R_1R_2CHCO-$ has the formula

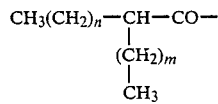

wherein n has a value of 5–15 and m has a value of 3–14.

19. The hair rinse composition of claim 3, wherein said quaternary ammonium salt has the formula $R_3R_4R_5R_6N^+X^-$ wherein 1 or 2 of the radicals $R_3$, $R_4$, $R_5$ and $R_6$ are $C_{8-22}$ long-chain alkyl $C_{8-22}$ hydroxyalkyl groups, and the remaining radicals are $C_{1-3}$ alkyl, $C_{1-3}$ hydroxalkyl, or benzyl groups, and X is a halogen atom or a $C_{1-2}$ alkyl sulfate.

* * * * *